United States Patent [19]

Woods et al.

[11] Patent Number: 4,469,787
[45] Date of Patent: Sep. 4, 1984

[54] IMMUNOASSAY INVOLVING SOLUBLE COMPLEX OF SECOND ANTIBODY AND LABELED BINDING PROTEIN

[75] Inventors: James W. Woods, Creve Coeur; John N. St. Denis, Maryland Hts.; Dana A. Chapman, Overland, all of Mo.

[73] Assignee: Mallinckrodt Inc., St. Louis, Mo.

[21] Appl. No.: 378,126

[22] Filed: May 14, 1982

[51] Int. Cl.$^3$ .................. G01N 33/54; G01N 33/56; G01N 33/58; G01N 33/76

[52] U.S. Cl. ........................................ 435/7; 422/61; 435/810; 436/500; 436/512; 436/534; 436/801; 436/804; 436/808; 436/813; 436/817; 436/818; 436/828

[58] Field of Search .................... 435/7, 810; 436/524, 436/828, 500, 512, 801, 804, 808, 813, 817, 818, 828, 534; 422/61

[56] References Cited

U.S. PATENT DOCUMENTS

| | | | |
|---|---|---|---|
| 3,791,932 | 2/1974 | Schuurs | 435/7 |
| 3,876,504 | 4/1975 | Koffler | |
| 3,966,898 | 6/1976 | Sjoquist | |
| 4,001,583 | 1/1977 | Barrett | |
| 4,067,959 | 1/1978 | Bolz | |
| 4,169,138 | 9/1979 | Jonsson | 436/524 |
| 4,200,508 | 4/1980 | Hirai | |
| 4,210,418 | 7/1980 | Brown | |
| 4,230,685 | 10/1980 | Senyei | |
| 4,230,797 | 10/1980 | Boguslaski | |
| 4,332,783 | 6/1982 | Pernice | 436/828 X |

OTHER PUBLICATIONS

G. W. Notani et al., J. Histochem. & Cytochem., 27(11), 1438–1444 (1979).

A. H. W. M. Schuurs et al., Clinica Chimica Acta, 81, 1–40 (1977).
R. H. Jacobson et al., Amer. Assn. Veterinary Diagnosticians, 21st Annual Proceedings, 367–376 (1978).
E. O'Keefe et al., J. Biol. Chem., 255(2), 561–568 (1980).
H. A. Erlich et al., "Methods in Enzymology", vol. 68, pp. 443–453, Academic Press, 1979.
A. Voller et al., Bull. World Health Organ., vol. 53, 55–65 (1976).
J. J. Langone et al., J. Immunol. Methods, 18, 281–293 (1977).
J. J. Langone, J. Immunol. Methods, 24, 269–285 (1978).
J. J. Langone, J. Immunol. Methods, 34, 93–106 (1980).
E. Engvall, Scand. J. Immunol. vol. 8, Suppl. 7, 25–31 (1978).

*Primary Examiner*—Sidney Marantz
*Attorney, Agent, or Firm*—Bernard, Rothwell & Brown

[57] ABSTRACT

A method and kit for determining the presence of a polyvalent ligand in an aqueous fluid. The method involves incubating the fluid with an immobilized antibody to the ligand to form an immobilized ligand-antibody complex, then incubating the immobilized ligand-antibody complex with a solution of a soluble complex of a second antibody (to the ligand) and a labeled binding protein, such as protein A. The labeled binding protein is specifically bound to the Fc portion of the second antibody. The unbound second antibody and labeled binding protein are washed from the immobilized complex, and the presence of bound labeled binding protein is determined as a measure of the concentration of the ligand in the aqueous fluid.

16 Claims, No Drawings

IMMUNOASSAY INVOLVING SOLUBLE COMPLEX OF SECOND ANTIBODY AND LABELED BINDING PROTEIN

BACKGROUND OF THE INVENTION

The present invention relates to a novel immunoassay. More particularly, the invention relates to an immunoassay which employs a labeled binding protein that nonspecifically binds with the $F_c$ portion of the IgG of several species and classes of immunoglobulins.

Immunoassays involving the specific interactions between antibodies, antigens, haptens, and other binding proteins have been widely employed for various analytical procedures, particularly in clinical laboratories. The sensitivity and specificity of immunological reactions permit their use in analytical procedures that require the differentiation of small concentrations of substances that are very similar in chemical structure. These assays are widely used in clinical situations for determining concentrations of enzymes, hormones, antibodies, antigens, and the like in biological fluids, for the diagnosis of numerous diseases and disorders. They are also employed for monitoring the concentrations of therapeutic drugs or for determining the presence of illicit drugs in fluids such as blood or urine.

The reaction between an antibody and an antigen or hapten (hereinafter collectively called a ligand) is generally not directly measurable. That is, the reaction product does not exhibit any physical or chemical properties that permit it to be distinguished from the unreacted materials, using conventional procedures. Therefore, one of the reactants is usually labeled in a way that permits its detection conveniently. For example, antibodies or ligands have been labeled with radioactive isotopes, such as $^{125}I$, tritium, $^{14}C$ and the like for use in radioimmunoassays. An important group of immunoassays is based on the use of an enzyme as a labeling substance. Enzymes can be covalently attached to an antibody or ligand in such a way that their enzyme activity is retained. The presence of an enzyme-labeled substance can be determined by the action of the enzyme on a substrate. Preferred enzyme substrates are those which, upon reaction with the enzyme, release a chromophore, i.e., a substance that absorbs visual or ultraviolet light or which fluoresces, and thus can be accurately measured using conventional analytical equipment. In addition to radioactive labels and enzyme labels, antibodies and ligands can also be labeled directly with chromogenic or fluorescent substances (e.g., fluorescein), as is known in the art.

A requirement that is common to each of these types of immunoassays is that the unbound labeled reactant be separated from the bound labeled reactant after the specific binding reaction has taken place. This separation is typically accomplished by fixing one or more of the reactants to a solid support. By this technique, the unbound labeled reactant can be eliminated from the system simply by washing it away from the solid support. Labeled reactant on the support or in the solution can then be determined quantitatively.

Immunoassays fall into two main categories: indirect or competitive assays and direct or sandwich assays. In a competitive assay, an analyte and a known concentration of a labeled analyte compete for a limited number of binding sites present on a solid surface which has been coated with the binding partner of the analyte. The amount of labeled reactant that binds to the solid surface is, therefore, inversely proportional to the concentration of analyte in the unknown sample. In a direct or sandwich assay, again, one reactant of the binding reaction is immobilized on a solid support. The other reactant, which is the analyte of interest, is exposed to the support under binding conditions, and therefore becomes immobilized by reaction with the bound material. A labeled material which is capable of binding to the immobilized analyte is then contacted with the solid surface and binds to the immobilized analyte in an amount directly proportional to the concentration of that analyte on the solid support.

A variety of solid supports have been devised for immunoassays. Such supports include the surfaces of plastic test tubes, polyacrylamide beads, plastic finned devices, latex particles, cellulose or glass fiber pads, and many others.

Essential elements of the above-described reactions are the labeled reactants. The preparation of these reactants is often a tedious and expensive procedure, and adds to the cost of the analytical system. Generally, the reactant to be labeled must be purified and reacted with the labeling substance by a relatively complex chemical reaction. Moreover, each labeled reactant is usually specific for a single test.

The requirement for a specific labeled reagent for each immunochemical test has been partially alleviated by the discovery of bacterial binding proteins that are capable of binding to the $F_c$ portion of immunoglobulins. The most widely used of such proteins is so-called protein A which is derived from the microorganism, *Staphylococcus aureus*. (See U.S. Pat. No. 3,966,898, Sjoquist, et al.) This protein has been found to bind to the $F_c$ or heavy chain portion of IgG immunoglobulins from a variety of species. The binding affinity of the protein is somewhat species selective, and within a species, can be selective for certain subclasses of IgG. For example, protein A has a very high affinity for subclasses 1, 2 and 4 of human IgG, a high affinity for all subclasses of rabbit IgG, a weak affinity for the IgG of goat, rat, sheep and mouse and negligible affinity for the IgG of chicken. As used herein, the term binding protein is meant to include protein A and proteins derived from microbial or other sources, having similar activities, as well as fragments of such proteins or polypeptides that have an affinity for the $F_c$ portion of certain IgG immunoglobulins, without affecting the specificity of the binding affinity of the $F(ab')_2$ portion of these immunoglobulins.

The specific binding affinity of such binding proteins permits those materials to be labeled and used in a wide variety of immunoassay systems, thereby eliminating the necessity for specifically labeled antibodies or ligands for each test. For example, Sjoquist, et al., supra describe direct immunoassays employing protein A labeled with a radioactive isotope or an enzyme. The assays involve first, binding an antigen to a solid support, then exposing the solid support to an IgG antibody for the antigen and finally exposing the immobilized antigen-antibody complex to labeled protein A. The test can be designed such that the amount of bound labeled protein A can be correlated to either the amount of antigen originally bound to the support or to the amount of antibody. A competitive type of immunoassay employing labeled protein A is described by John J. Langone, et al. (*Journal of Immunological Methods*, 18, 281–283 (1977); 24, 269–285 (1978); and 34, 93–106

(1980)). That system also involves binding a ligand to a solid support, then exposing that support to an antibody to the ligand and then to labeled protein A. Ligand in solution can compete with bound ligand for the antibody binding sites, and therefore, the amount of labeled protein A that binds to the solid support is an indirect measure of the concentration of ligand in solution.

In each of the above-described procedures, it is necessary for the antigen to be bound to the solid support initially, so that only one IgG antibody need be employed. Erlich, Henry A., et al., *Methods in Enzymology*, 68, 443-453 (1979) describe a direct immunoassay for products translated from cloned DNA fragments, which employs radio-labeled protein A as a tracer. In this method, an antibody is immobilized on a solid support and a sample containing an antigen to the antibody is exposed to the support under conditions that permit the antigen to bind to the antibody and thereby be immobilized. The solid support is then exposed to a second antibody which binds to the immobilized antigen, and finally the solid support is exposed to the radiolabeled protein A which binds to the $F_c$ portion of the second antibody. In the described procedure, the first antibody is digested with the proteolytic enzyme, pepsin, to remove its $F_c$ portion prior to attachment to the solid support. The reason for this digestion is to eliminate the possibility that the labeled protein A will bind to the first antibody, and thereby create a high level of background signal.

A need exists for a method of conducting direct, two site immunoassays, using labeled binding protein as a tracer, without requiring the removal of the $F_c$ portion of either of the antibodies.

SUMMARY OF THE INVENTION

In accordance with the present invention, a method for quantitatively determining the presence of a polyvalent ligand in an aqueous fluid involves the steps of
  (a) incubating said fluid with a solid support having first antibody to said ligand bound thereto to form an immobilized antibody-ligand complex;
  (b) incubating said immobilized-antibody-ligand complex with a solution containing a soluble complex of a second antibody to said ligand and a labeled binding protein that specifically binds to the $F_c$ portion of said second antibody;
  (c) separating unbound antibody and labeled binding protein from the solid support; and
  (d) determining the presence of labeled binding protein either bound to said solid support or remaining in solution as a measure of the concentration of the ligand in the aqueous fluid;
whereby said method is further characterized in that the solution of second antibody-labeled binding protein complex contains an excess concentration of second antibody to provide a substantially linear relationship between the amount of bound labeled binding protein and the concentration of the ligand in the aqueous fluid, while maintaining a low level of background signal.

In a particular embodiment, prior to immobilization of the first antibody on the solid support, it can be enzymatically digested to remove the Fc binding fragment. In this embodiment, the second antibody-labeled binding protein complex is preferably constructed at or near stoichiometric equivalence (i.e., molar ratio of second antibody to labeled binding protein is about 2:1).

DETAILED DESCRIPTION OF THE INVENTION

The present invention involves a direct, two-site immunoassay employing labeled binding protein as a tracer, in which a first antibody can be immobilized on a solid support in either intact or digested form. It has been discovered that the need for enzymatically removing the $F_c$ portion of the first antibody in such an assay is obviated, if a complex composed of labeled binding protein and soluble second antibody is formed in solution, as hereinafter described.

The general assay system involves immobilizing a first antibody to the ligand of interest on a solid support. The solid support is then exposed to a standard or sample solution which contains or is suspected of containing the ligand. An excess of binding sites are present on the solid support, so that substantially all of the ligand in the standard or sample solution binds with the immobilized first antibody. The remaining solution is then advantageously washed or otherwise removed from the solid support prior to succeeding steps. The solid support is then exposed to a solution containing a soluble complex of the second antibody to the ligand of interest and a labeled binding protein, preferably protein A, which is bound to the Fc portion of the second antibody. This complex binds to the immobilized ligand in an amount directly proportional to the amount of ligand present on the support surface. Unbound labeled binding protein-antibody complex may then be washed from the solid support, and either the amount of labeled binding protein immobilized on the support or the amount of labeled binding protein remaining in solution can be determined, and that amount can be correlated to the concentration of ligand in the original solution.

Since the first antibody can be an intact IgG immunoglobulin to which the labeled binding protein has a binding affinity, this scheme is somewhat complicated by side reactions. It has been found that free binding protein will combine with the first antibody immobilized on the solid support, whether or not the immobilized antibody has reacted with the ligand. These false binding events result in an unacceptably high background signal. For this reason, previous attempts to develop direct two-site immunoassays employing protein A, have required the enzymatic digestion of the first antibody to remove its Fc portion prior to immobilization.

It has now been found that when the labeled binding protein for such an immunoassay is provided as a soluble complex with the second antibody, these false binding events can be significantly reduced. To maintain the labeled binding protein in the complexed, rather than free form, an excess of second antibody is provided in the solution of labeled binding protein-second antibody complex. When very high concentrations of soluble second antibody (relative to the concentration of labeled binding protein) are employed, false binding events can be substantially eliminated, thereby reducing background to a very low level. However, in such a situation, the sensitivity of the reaction also suffers. At the opposite extreme, when very low concentrations of soluble second antibody are employed there is a substantial tendency for labeled binding protein to bind not only to the second antibody, but also to the immobilized first antibody. This situation results in a non-linear response-concentration relationship, and also introduces an unacceptable level of background signal due to false binding events, resulting in substantially reduced sensitivity. The foregoing relationships are represented by the following formulas:

Note:
BP* = labeled binding protein

Equation (1) represents the competition of labeled binding protein for solid supported first antibody and soluble second antibody. As the soluble second antibody concentration is increased, the potential for binding to supported first antibody ("false binding") is reduced. Equation (2) represents the competition for bound ligand between a soluble second antibody - binding protein complex and a soluble second antibody deficient of binding protein label. In the immunoassay of the present invention, excess second antibody is employed to reduce false binding, and therefore it is expected that some fraction of this antibody will bind to the ligand, but recognition of these binding events will not be indicated for lack of binding protein label.

The present invention involves exposing the immobilized ligand to a solution containing a complex of second antibody and labeled binding protein, wherein the relative concentrations of those reactants is controlled to provide a sensitive and substantially linear concentration response relationship, while also providing an analytically acceptable low level of background signal. The relative concentrations of soluble second antibody and labeled binding protein can be determined empirically for each particular system as is described hereinafter in the specific examples. The molar ratio of reactant concentrations will vary depending upon the type of solid support employed and the number of Fc binding sites occurring on such support, the binding affinities of the various reactants, and the particular ligand for which the assay is designed. Generally, the molar ratio of soluble second antibody to labeled binding protein will range from about 50:1 to about 24,000:1, and preferably ranges from about 250:1 to about 5000:1.

In the case where the assay employs enzymatically digested first antibody, the relationship repesented in Equation (1) above is inapplicable, because of the absence of Fc binding sites on the solid supported first antibody. In that embodiment, it is preferred that the conditions represented in Equation (2) be optimized, such that substantially all second antibody species in the second antibody-labeled binding protein complex, be associated with labeled binding protein. Such optimization can be achieved by adjusting the relative molar concentrations of soluble second antibody and labeled binding protein in the range of from about 500:1 to about 1:1.

As can be seen from the above discussion, to be subject to assay by a two site method, a ligand is advantageously polyvalent, that is, at least divalent. Polyvalent ligands have at least two binding sites which permit the ligand to simultaneously bind to solid phase antibody and soluble antibody. Some common analytes, such as certain therapeutic drugs, are not polyvalent antigens, but in certain cases can be converted to polyvalent ligands by reacting them with another substance, as is well known in the art.

The method of the present invention is not limited to any particular form of solid support. Conventional supports include coated tubes (U.S. Pat. No. 3,867,517), sponge like materials (U.S. Pat. No. 3,951,748), plastic inserts (U.S. Pat. No. 3,826,619), finned inserts (U.S. Pat. No. 4,135,884 and U.S. Pat. No. 4,225,575), plastic beads (U.S. Pat. No. 3,932,141) and discs (Catt, K., et al. *J.Lab.&Clin.Med.*, 70, 820-830 (1967)). Immunobeads (carboxyl functionalized polyacrylamides, available from Bio-Rad Laboratories, Richmond, Calif.), and the like can be employed in the present method. Plastic beads, such as polystyrene beads, are preferred for the method of the present invention, wherein either whole first antibodies (IgG) or enzymatically digested antibody fragments (F(ab')$_2$) are used.

The first antibody can be coupled to the solid support by any of a number of well known procedures. With some materials, it is only necessary to incubate the antibody with the solid support to form a weak absorbtive bond between the two.

It will be understood that the conditions and procedures for the binding reactions as well as the procedures for labeling the binding protein employed in the present invention are well recognized in the art.

By selecting the appropriate reactants, the method of this invention can be readily adapted to the determination of a wide variety of tests. For example, any protein or polypeptide antigen, including, but not limited to ferritin, thyroid stimulating hormone, creatinine phosphokinase, prostatic acid- phosphatase, human chorionic gonadotrophin, alpha fetoprotein (AFP), parathyroid hormone (PTH), insulin, C-peptide, and the like can be determined.

Also contemplated within the present invention are clinical assay test kits for determining the presence of various analytes in biological fluids such as blood, serum, tissue homogenates, or urine. Such test kits generally comprise a solid support coated with an antibody for the particular ligand of interest, and in a separate container a solution containing a second antibody to such ligand complexed with a labeled binding protein. In the case of an enzyme immunoassay, the test kit also advantageously contains a solution of a chromogenic substrate for detecting the labeled binding protein. Such a test kit can conveniently be employed by the clinical analyst for carrying out the desired assay. For example, the analyst generally delivers a small volume of the sample fluid and a suitable buffer to the solid support and incubates to effect the first binding reaction. The solid support is normally then washed with additional buffer solution and placed in the second antibody-labeled binding protein complex solution and again incubated. In the case of a radioimmunoassay, the solid support is then placed in a gamma counter, and the counts taken for comparison to a standard calibration curve. In the case of an enzymeimmunoassay, the solid support is placed in a solution of the chromogenic enzyme substrate, and the resulting chromophore is measured spectrophotometrically or fluorometrically. In addition to manual test kits, test kits for use in various automated clinical analyzers can also be conveniently provided.

The present invention is further illustrated by the following examples, which are not intended to be limiting.

EXAMPLE I

The following example describes the conditions for formation of a Protein A-$I^{125}$/rabbit anti-ferritin IgG complex and its use in a radioimmunoassay for ferritin.

Complex Formation: Rabbit anti-ferritin IgG, isolated from whole sera, of a desired concentration in 0.02 M phosphate buffer (pH 7.4, 0.1% BSA, 0.1% NaN$_3$) is combined with a solution of Protein A-$I^{125}$ (obtained from Amersham, Arlington Heights, Ill.) of the desired concentration in 0.02 M phosphate buffer (pH 7.4, 0.1% BSA, 0.1% NaN$_3$) and incubated for one hour at 37° C. For this example, three such solutions were prepared with molar ratios of rabbit anti-ferritin IgG to Protein A-$I^{125}$ as shown in Table I.

Radioimmunoassay

The procedure employed polystyrene bead (0.25 inches diameter) supported rabbit anti-ferritin (IgG) antibody obtained from a ferritin radioimmunoassay kit marketed by Ramco Laboratories, Houston, Tex. To a set of test tubes were added aliquots (10 ul) of ferritin standard solutions with ferritin concentrations as shown in Table I. The liquid volumes in each tube were made up to 210 ul with the addition of 200 ul of 0.02 M phosphate buffer (pH 7.4, 0.1% BSA, 0.1% NaN$_3$). A polystyrene bead was added to each tube, and the tubes were incubated for three hours at 37° C. The solid support was then washed three times with the 0.02 M phosphate buffer. To each tube was then added an aliquot (200 ul) of a solution containing the rabbit anti-ferritin IgG/Protein A-$I^{125}$ complex. The tubes were incubated for one and one-half hours at 37° C. and the solid support was washed three times with the 0.02 M phosphate buffer. The polystyrene beads were individually transferred to clean test tubes and placed in a gamma counter and the bound radioactivity measured. The results are shown in Table I. An analysis of this data indicates that for those tubes having a soluble IgG/PA $I^{125}$ ratio of 25,000:1, the sensitivity was limited and for tubes having a soluble IgG/PA $I^{125}$ ratio of 250:1, background was excessive and a non-linear response was observed. For those tests having a soluble IgG/PA $I^{125}$ ratio of 2500:1, a substantially linear response was obtained up to a concentration of 600 ng/ml with non-interferring background levels.

EXAMPLE II

The experiment of Example I was repeated in all essential details except that soluble rabbit anti-ferritin IgG concentrations were 300 micrograms per milliliter, 60 micrograms per milliliter, 6 micrograms per milliliter and 3 micrograms per milliliter, and an alkaline phosphatase-protein A conjugate purchased from Zymed Laboratories, Burlingame, Calif., was substituted for radiolabeled protein A and used at a dilution of 1:1000 in 0.02 M phosphate buffer (pH 7.4, 0.1% BSA, 0.1% NaN$_3$). Following the second antibody/protein A-alkaline phosphatase complex incubation period and wash sequence, the solid supports were transferred to clean tubes and incubated at 37° C. in 0.1 M glycine, pH 10.4, containing 1 mM magnesium chloride and 2 mg/ml p-nitrophenylphosphate (200 ul). The enzyme reaction was terminated after 20 minutes of incubation with 1.0 milliliters of 0.5 molar sodium hydroxide, and optical density measurements were made at 405 nm. The results are shown in Table II. Again, low concentrations of soluble IgG produced high levels of background signals, and high concentrations of soluble IgG resulted in limited sensitivity. A soluble IgG concentration of 60 micrograms per milliliter resulted in linear assay results having low levels of background interference.

EXAMPLE III

The experiment of Example I was repeated in all essential details except that enzymatically digested rabbit anti-ferritin IgG was used as first antibody on polystyrene beads. Soluble rabbit anti-ferritin IgG/Protein A-$I^{125}$ complexes were formulated to yield the molar ratios given in Table III. The results of the experiment are also shown in Table III. An analysis of this data shows that improved sensitivities and linear responses are achieved by proper adjustment of the soluble rabbit anti-ferritin IgG/labeled protein A molar ratio. When the assay is conducted with enzyme-digested first antibody, sensitive, linear results are obtained with substantially lower molar ratios (approaching stoichiometric unity) of second antibody to labeled Protein A as compared to assays employing whole first antibodies.

EXAMPLE IV

The experiment of Example II was repeated in all essential details except that enzyme-digested rabbit anti-ferritin IgG was used as first antibody on polystyrene beads. Soluble rabbit anti-ferritin IgG concentrations were as shown in Table IV.

TABLE I

| | Bound Protein A (I-125) on Supported Rabbit Anti-Ferritin IgG | | |
|---|---|---|---|
| | CPM (Avg.) | | |
| Ferritin Std. | Rabbit anti-ferritin IgG/PA-$I^{125}$(Molar)* | | |
| (ng/ml) | 25,000/1 | 2,500/1 | 250/1 |
| 0 | 175 | 516 | 1193 |
| 6.0 | 157 | 606 | 1725 |
| 20.0 | 209 | 695 | 1882 |
| 60.0 | 369 | 1051 | 2558 |
| 200.0 | 620 | 1964 | 3898 |
| 600.0 | 1166 | 3189 | 4725 |
| 2000 | 2003 | — | 5169 |

*A constant Protein A-$I^{125}$ concentration (3.2 ng/ml) was used throughout. Rabbit anti-ferritin IgG concentrations were 300 ug/ml, 30 ug/ml and 3 ug/ml. These correspond to molar IgG/Protein A $I^{125}$ ratios of 25,000/1, 2500/1 and 250/1, respectively.

TABLE II

| | Bound Protein A-Alkaline Phosphatase on Supported Rabbit Anti-Ferritin IgG | | | |
|---|---|---|---|---|
| | Optical Density$_{405}$ | | | |
| Ferritin Standard | Rabbit anti-ferritin IgG (ug/ml) | | | |
| (ng/ml) | 300 | 60 | 6 | 3 |
| 0 | 0 | 0 | .025 | .060 |
| 6.0 | 0 | 0 | .028 | .072 |
| 20.0 | 0 | .006 | .062 | .096 |
| 60.0 | .002 | .026 | .108 | .143 |
| 200.0 | .014 | .088 | .190 | .241 |
| 600.0 | .065 | .176 | .301 | .318 |

TABLE III

| | Bound Protein A (I-125) on Supported Rabbit Anti-Ferritin F(ab')$_2$ | | |
|---|---|---|---|
| | CPM (Avg.) | | |
| Ferritin Standard | Rabbit anti-ferritin IgG/PA-$I^{125}$ (Molar)* | | |
| (ng/ml) | 597/1 | 119/1 | 60/1 |
| 0 | 800 | 776 | 785 |

TABLE III-continued

Bound Protein A (I-125) on Supported Rabbit Anti-Ferritin F(ab')₂

| Ferritin Standard | CPM (Avg.) Rabbit anti-ferritin IgG/PA-I$^{125}$ (Molar)* | | |
|---|---|---|---|
| (ng/ml) | 597/1 | 119/1 | 60/1 |
| 6.0 | 731 | 869 | 953 |
| 20.0 | 830 | 1102 | 1132 |
| 60.0 | 1613 | 2136 | 1970 |
| 200.0 | 4208 | 4778 | 4622 |
| 600.0 | 8003 | 8655 | 7212 |

*A constant Protein A-I$^{125}$ concentration (8.8 ng/ml) was used throughout. Rabbit anti-ferritin IgG concentrations were 2.0 ug/ml, 4.0 ug/ml and 2.0 ug/ml. These concentrations correspond to molar IgG/Protein A$^{125}$ ratios of 597/1, 119/1 and 60/1, respectively.

TABLE IV

Bound Protein A-Alkaline Phosphatase on Supported Rabbit Anti-Ferritin F(ab')₂

| Ferritin Standards | OD$_{405}$ Rabbit Anti-Ferritin IgG (μg/ml) | | |
|---|---|---|---|
| (ng/ml) | 20.0 | 10.0 | 2.0 |
| 0 | .026 | .018 | .021 |
| 6 | .026 | .028 | .022 |
| 20 | .035 | .053 | .041 |
| 60 | .116 | .115 | .111 |
| 200 | .389 | .381 | .410 |
| 600 | .907 | 1.11 | .910 |

We claim:

1. A method for quantitatively determining the presence of polyvalent ligand in an aqueous fluid which comprises:
   (a) incubating said fluid with a solid support having a first antibody to said ligand bound thereto to form an immobilized antibody-ligand complex;
   (b) incubating said immobilized antibody-ligand complex with a solution containing a soluble complex of a second antibody to said ligand and a labeled binding protein specifically bound to the $F_c$ portion of said second antibody;
   (c) washing unbound antibody and labeled binding protein from the solid support; and
   (d) determining the presence of labeled binding protein bound to said solid support or remaining in solution, as a measure of the concentration of the ligand in the aqueous fluid;
   wherein said method is further characterized in that the solution of second antibody-labeled binding protein complex contains an excess concentration of second antibody to provide a substantially linear relationship between the concentration of ligand and the amount of labeled binding protein bound to the solid support, while maintaining analytically acceptable low levels of background interference.

2. The method of claim 1, wherein the molar ratio of soluble second antibody to labeled binding protein is from about 250:1 to about 5,000:1.

3. The method of claim 1, wherein the molar ratio of soluble second antibody to labeled binding protein is from about 50:1 to about 24,000:1.

4. The method of claim 3, wherein the labeled binding protein is protein A obtained from *Staphylococcus aureus*.

5. The method of claim 4, wherein the ligand is ferritin.

6. The method of claim 4, wherein the ligand is selected from the group consisting of ferritin, thyroid stimulating hormone, creatinine phosphokinase, prostatic acid-phosphatase, and human chorionic gonadotroin, alpha fetoprotein, parathyroid hormone, insulin and C-peptide.

7. The method of claim 6, wherein the first antibody is an intact antibody.

8. The method of claim 5 or 6, wherein the labeled binding protein is selected from the group consisting of $^{125}$I-Protein A, $^3$H-Protein A and $^{14}$C-Protein A.

9. The method of claim 5 or 6, wherein the labeled binding protein is enzyme-labeled Protein A.

10. The method of claim 5 or 6, wherein the labeled binding protein is protein A labeled with a fluorescent substance.

11. An immunoassay test kit for determining the presence of a ligand in an aqueous fluid comprising a solid support coated with an antibody to said ligand and, in a separate container, a solution containing a soluble complex of a second antibody to said ligand and a labeled binding protein, wherein the concentrations of second antibody and labeled binding protein in said solution are in a molar ratio of from about 50:1 to about 24,000:1 respectively.

12. The test kit of claim 11, wherein the molar ratio of second antibody to labeled binding protein is from about 250:1 to about 5,000:1.

13. The test kit of claim 12, wherein the labeled binding protein is radiolabeled Protein A.

14. The test kit of claim 12, wherein the labeled binding protein is enzyme-labeled Protein A, and said test kit further comprises a solution of a chromogenic substrate for said enzyme.

15. A method for quantitatively determining the presence of polyvalent ligand in an aqueous fluid which comprises:
   (a) incubating said fluid with a solid support having a first antibody to said ligand bound therto to form an immobilized antibody-ligand complex;
   (b) incubating said immobilized antibody-ligand complex with a solution containing a soluble complex of a second antibody to said ligand and a labeled binding protein specifically bound to the Fc portion of said second antibody;
   (c) washing unbound antibody and labeled binding protein from the solid support; and
   (d) determining the presence of labeled binding protein bound to said solid support or remaining in solution, as a measure of the concentration of the ligand in the aqueous fluid;
   wherein said method is characterized in that the first antibody is an IgG immunoglobin which has been enzymatically digested to remove the Fc portion.

16. The method of claim 15, wherein the molar ratio of soluble second antibody to labeled binding protein is from about 500:1 to about 1:1.

* * * * *